United States Patent [19]

Arroyo et al.

[11] 4,388,410
[45] Jun. 14, 1983

[54] METHOD TO DETERMINE CARBON BLACK CONTENT

[75] Inventors: Nestor A. Arroyo, Cranbury; Nitin V. Desai, Hightstown, both of N.J.; James F. Buchanan, Greenwood, Ind.

[73] Assignee: RCA Corporation, New York, N.Y.

[21] Appl. No.: 223,856

[22] Filed: Jan. 9, 1981

[51] Int. Cl.³ .................. G01N 25/00; G01N 33/44
[52] U.S. Cl. ................................ 436/85; 436/126; 436/157; 436/908
[58] Field of Search ................ 23/230 M, 230 PC; 436/85, 126, 157, 908

[56] References Cited

PUBLICATIONS

Thermochimica Acta 26 (1978), 349-359-Schwartz et al.
Microprocessor-Controlled Thermogravimetric Separations, Cassel et al., Thermochim. Acta. 36, 3, 265-77, 1980.
Charsley et al., Plast. Rubber Process Appl., 81, 1(1), 3-7.
Collins-"Application of Thermal Analysis to the Study of Elastomers", Characterization of Thermoplastic Polymers, E. I. DuPont, 1970.

Primary Examiner—Michael S. Marcus
Attorney, Agent, or Firm—Birgit E. Morris; R. Hain Swope

[57] ABSTRACT

A method for thermogravimetrically analyzing a plastic molding composition comprising carbon black and a vinyl chloride homopolymer or copolymer molding resin to determine the carbon black content wherein the method comprises the steps of compounding the molding composition so that the carbon black is uniformly dispersed therein, heating the molding composition in an inert atmosphere to a temperature sufficient to reproducibly thermally decompose the vinyl chloride homopolymer or copolymer, maintaining the molding composition at the decomposition temperature in an inert atmosphere for a first given time which is long enough so that there is no further significant weight loss, weighing the molding composition to determine the weight loss during the first given time and comparing the weight loss for the first given time with that for samples of known composition analyzed under the same conditions to determined the carbon black content of the molding composition.

9 Claims, 1 Drawing Figure

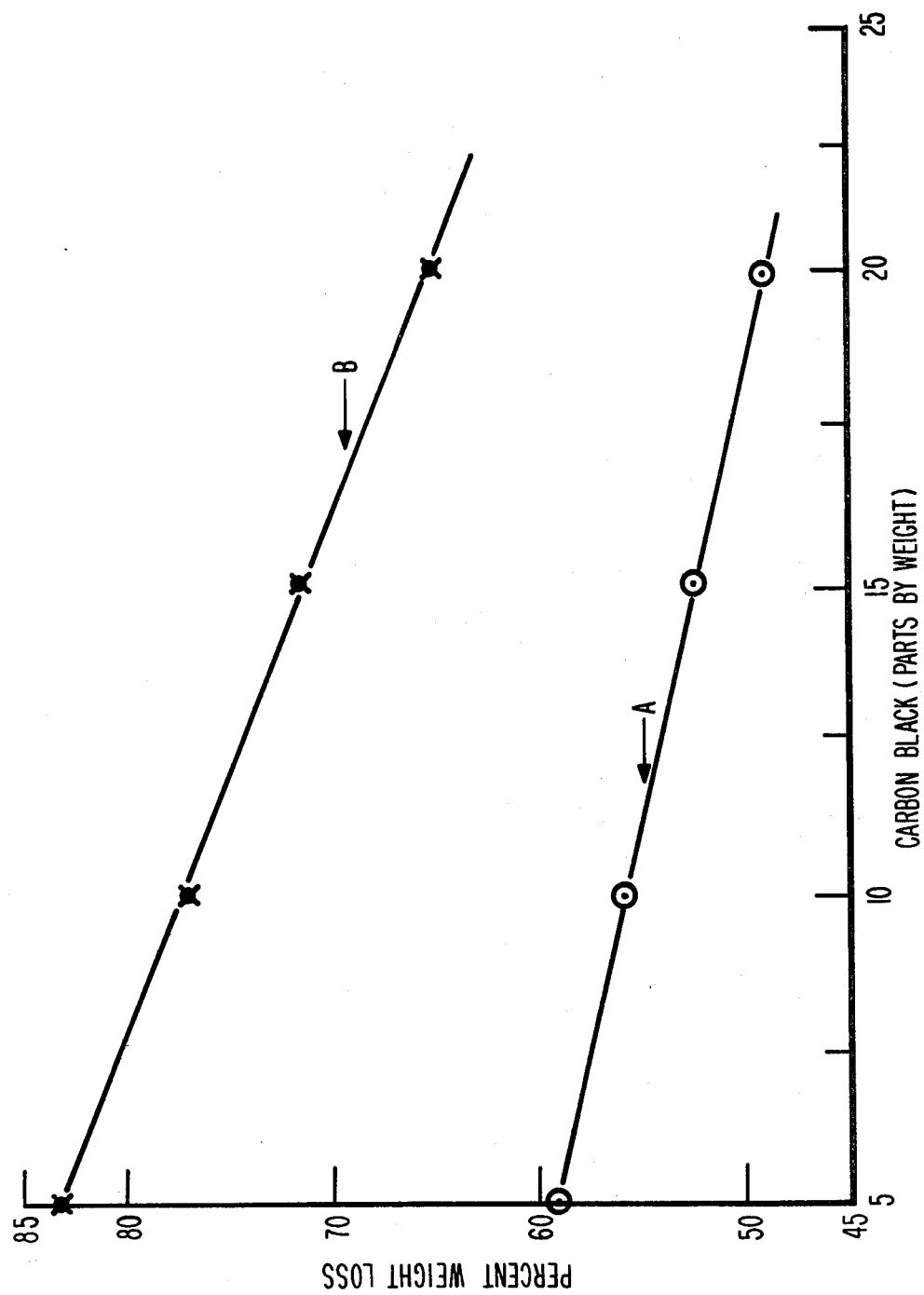

METHOD TO DETERMINE CARBON BLACK CONTENT

This invention relates to a method for determining carbon black content. More particularly, this invention relates to a thermogravimetric method for determining the amount of carbon black in a plastic moulding composition or an article such as a capacitive information disc record prepared therefrom.

BACKGROUND OF THE INVENTION

A capacitance information recording and playback system has been disclosed by Clemens in U.S. Pat. Nos. 3,842,194, 3,842,217 and 3,909,517. In this system, a plastic disc record is prepared having geometric variations in a spiral groove in a disc surface which variations represent audio and video information. The disc record is coated with a conductive layer and a dielectric layer. A stylus having a conductive electrode is used to reconstitute the information as an electrical signal.

Other systems have been devised based on a capacitance readout in which the disc record does not require a grooved surface. In either the grooved or the non-grooved system a further improvement has been made whereby conductive plastic molding composition may be employed to form the disc record, thereby eliminating the need for separate conductive and dielectric layers.

Generally, the conductive disc records are prepared from a plastic molding composition containing conductive particles (e.g., carbon black), a molding resin such as a vinyl chloride homopolymer or copolymer and various additives such as lubricants, stabilizers, flow modifiers, and the like.

In a manufacturing environment where thousands of disc records are produced daily, a fast and reliable quality control method is required to analyze the carbon black content of the plastic molding composition as well as the disc records molded therefrom.

SUMMARY OF THE INVENTION

We have found a method for thermogravimetrically analyzing a plastic molding composition comprising carbon black and a vinyl chloride homopolymer or copolymer molding resin to determine the carbon black content wherein the method comprises compounding the molding composition so that the carbon black is uniformly dispersed therein, heating the molding composition in an inert atmosphere to a temperature sufficient to reproducibly thermally decompose the vinyl chloride homopolymer or copolymer, maintaining the molding composition at the decomposition temperature in an inert atmosphere for a first given time which is long enough so that there is no significant further weight loss, weighing the molding composition to determine the weight loss during the first given time and comparing the weight loss during the first given time with that for samples of known composition analyzed under the same conditions to determine the carbon black content of the molding composition.

BRIEF DESCRIPTION OF THE DRAWING

The FIGURE is a graph of precent weight loss for a given time as a function of carbon black composition for samples of known composition.

DETAILED DESCRIPTION OF THE INVENTION

This method is based on the specific thermal degradation of plastic molding compositions and products obtained therefrom where the components include carbon black and a vinyl chloride homopolymer or copolymer molding resin. Various flow modifiers, stabilizers, lubricants, and the like may also be present.

To compound the plastic molding composition, heat and a shearing force must be concurrently applied. The purpose of compounding is to uniformly disperse the carbon black throughout the molding composition. The heat applied must be sufficient to fuse the molding resin. For example, a two-roll mill or an extruder may be employed for compounding. Unless compounding is performed prior to thermogravimetric analysis, the sample chosen for analysis may be unrepresentative of the batch from which it is taken. If a molded article is being analyzed, no additional compounding is needed if the plastic molding composition was compounded in the course of manufacturing the article.

In one embodiment of the present invention the plastic molding composition sample after compounding is heated to about 350° C. in an inert atmosphere such as nitrogen, argon and the like. At this stage, the polymerized vinyl chloride moiety dehydrochlorinates with a concurrent loss of weight primarily as HCl. The sample is kept at about 350° C. for a given time which is long enough so that there is no significant further weight loss. The total weight loss during the given time is monitored. The weight loss has been found to be a function of the relative amounts of carbon black and polymerized vinyl chloride initially present in the plastic molding composition when the sum of the parts by weight of these components is constant. The larger the relative amount of carbon black, the smaller the observed weight loss. The resulting crosslinked polymeric resin most probably contains conjugated double bonds and its elemental constituents are primarily carbon and hydrogen. This embodiment is particularly useful when information regarding a molding resin's structure is wanted.

In a further thermogravimetric step, the sample may then be heated to a temperature between about 600° and 750° in an inert atmosphere. The sample is maintained at this temperature for a specific time which is long enough so that there is no further significant weight loss. The total weight loss during the specific time is determined. Again, the weight loss has been found to be a function of the relative amounts of carbon black and polymerized vinyl chloride initially present in the plastic molding composition when the sum of the parts by weight of these ingredients are a constant. The larger the relative amount of carbon black, the smaller the weight loss. The weight loss in the 600°–750° range is more sensitive to the carbon black content than the weight loss at 350° C.

In the 600°–750° C. range, it is believed that the molding resin carbonizes, losing its remaining hydrogen, and is transformed into a compact carbon mass. The carbon mass is composed of the carbon black initially present as well as the carbon produced primarily by the carbonization of the molding resin as well as by the other organic constituents. For rapid analysis, the plastic molding composition sample to be analyzed may be directly heated to a temperature between about 600° and 750° C. in an inert atmosphere and maintained at that temperature for a time which is long enough so that there is no further significant weight loss.

In an optional further thermogravimetric step the carbon mass is oxidized in an oxidizing atmosphere, such as oxygen or air, at a temperature between about 600° and 750°. in order to determine the amount of carbon present. In this reaction, the carbon oxidizes to form primarily carbon dioxide leaving a residue of inorganic ash. Again at this stage, the weight loss during the oxidation step is monitored. Different sources of carbon black can result in different amounts of residual ash.

The weight loss at about 350° C. or at the temperature in the about 600°–750° C. range for each step of the analysis is compared with standard curves obtained by running samples having known compositions at the same temperatures and the same times. Minor variations in the molding composition, particulary with regard to the lubricants, stabilizers, flow modifiers, and the like, have little effect upon the determination of carbon black content. By comparing the weight loss of a sample under investigation at the temperatures and conditions heretofore described with a sample of known composition, the amount of carbon black present may be determined.

When heating is required, the samples are generally heated at a rate preferably of between about 40° and 200° C. per minute, more preferably between about 160° and 200° C. per minute. At slower heating rates, the time required for analysis may be unnecessarily long. At higher heating rates, samples may not be heated uniformly which leads to results which are not reproducible. Furthermore, a portion of the sample may be lost due to ejection by hot spot formation.

It has also been found advantageous to preheat a sample at 50° C. in an inert atmosphere for a short time period, preferably about one minute. This preheating step allows the removal of volatiles such as trace amounts of solvents and moisture which may be present and which may lead to irreproducible or inaccurate results.

The sample size may be any convenient weight. If the sample is too light, the measured changes in weight may be unreliable. The sample to be analyzed should be compressed so that a larger sample weight may be analyzed. If the sample is too heavy, portions of the sample may not react fully unless an extended heating time and relatively slow heating rate are employed. In general, a sample weight of between about 5 and 35 milligrams has been found to be suitable.

The present invention may be carried out with a commercially available thermogravimetric analyzer. An analyzer equipped with a microprocessor control allows for convenient measurement and data handling.

The prior art method of determining the amount of carbon black loading of filled plastics is to completely decompose the plastic so that there is no residue and then to determine the amount of carbon black present by thermally oxidizing the carbon black to $CO_2$ and measuring the weight loss due to $CO_2$ evolution. Such a method is not applicable to a plastic molding composition comprising a vinyl chloride homopolymer or copolymer because of the incomplete decomposition of the resin which results in a residue which does not allow the determination of carbon black by oxidation.

Vinyl chloride-containing polymers are known to thermally decompose at about 200° C. The presence of stabilizers in the composition inhibits the decomposition so that a sample must be heated for a longer period before decomposition of the polymer begins. The longer period is apparently necessary because the stabilizers must be used up before the normal polymer decomposition takes place.

The decomposition of vinyl chloride-containing polymers at about 200° to 250° C. cannot be used to determine carbon black loading. Although this temperature range is normally employed for thermogravimetric studies, it has been found that the results are not sufficiently reproducible for the present purposes. Instead a temperature of about 350° C. must be used. Similarly, while it is known that the final decomposition of vinyl chloride-containing polymers in an inert atmosphere is generally complete at 500° to 550° C., it has been found that thermogravimetric results obtained in that range are not sufficiently reproducible for the present purposes. Thus, a higher temperature in the range of about 600°–750° C. is required although decomposition should be complete in the 500°–550° C. region.

This invention will be further illustrated by means of the following Examples. However, it is to be understood that the details therein are not meant to thereby limit the invention.

EXAMPLE I

For each run, compounded pressed pellet samples of one of the plastic molding compositions shown in Table I were placed in the furnace of a thermogravimetric balance (Perkin Elmer Model TGS-2 Thermogravimetric System) which was at room temperature.

TABLE I

| Run | Carbon Black (parts by weight) | Poly(vinyl chloride) (parts by weight) | Additives (parts by weight) |
|---|---|---|---|
| 1 | 15 | 75 | 10 |
| 2 | 13 | 77 | 10 |
| 3 | 10 | 80 | 10 |

The compositions were compounded in a Banbury Plasticorder mixer by melting each composition under shear using a temperature range of 300° to 370° F. (149°–184° C.) during the steps of the compounding process. The temperature range was sufficient to fuse the molding resin.

The pressed pellet was heated at 50° C. for one minute in a nitrogen atmosphere. No weight loss was observed. While maintaining the nitrogen atmosphere, the temperature was raised at 350° C. at a rate of 200° per minute and, for step 1, the sample was held at 350° C. for 10 minutes. While maintaining the nitrogen atmosphere, the temperature was increased to 600° C. at a rate of 200° C. per minute and, for step 2, the sample was held at 600° C. for 5 minutes. The atmosphere was changed to oxygen and, for step 3, the sample was held at 600° C. for about 9 minutes.

For each run, the amount of material lost after each step is shown in Table II.

TABLE II

| | Step 1 | Step 2 | Step 3 |
|---|---|---|---|
| Material Lost in Run 1 (% of the starting weight) | 54.0 | 72.5 | 93.4 |
| Material Lost in Run 2 (% of the starting weight) | 54.8 | 74.0 | 99.5 |
| Material Lost in Run 3 (% of the | 57.0 | 77.5 | 99.5 |

TABLE II-continued

|  | Step 1 | Step 2 | Step 3 |
|---|---|---|---|
| starting weight) | | | |

The results for steps 1 and 2 indicate that the weight loss is inversely proportional to the starting amount of carbon black if the other components of the sample are kept constant with the exception of the poly(vinyl chloride). The sum of the parts by weight of the carbon black and poly(vinyl chloride) were kept constant. The results for step 3 may be used to determine the residual inorganic ash content of the sample. For Run 1, the carbon black was Cabot CSX-150 (available from the Cabot Corp.); for Runs 2 and 3 the carbon black was Ketjenblack EC (available from Akzo Chemie). Runs 2 and 3 had a residual ash content of 0.5% while Run 1 had a residual ash content of 1.6%.

EXAMPLE II

The procedure of Example I was repeated using samples of known composition as shown in Table III.

TABLE III

| Run | Carbon Black (parts by weight) | Poly (vinyl chloride) (parts by weight) | Additives (parts by weight) | Material lost in Step 1 (% of starting weight) | Material lost in Step 2 (% of starting weight) |
|---|---|---|---|---|---|
| 1 | 5 | 86 | 9 | 59.0 | 83.0 |
| 2 | 10 | 81 | 9 | 56.0 | 77.0 |
| 3 | 15 | 76 | 9 | 52.4 | 72.5 |
| 4 | 20 | 71 | 9 | 49.0 | 65.0 |

The weight loss for steps 1 (heating at 350° C. for 10 minutes) and 2 (heating at 600° C. for 5 minutes) are shown in Table III and graphically in the FIGURE as lines A and B, respectively. The percentage weight loss varies inversely with the carbon black content of the sample. The sensitivity of the weight loss to carbon black content is greater at 600° C. than at 350° C.

When a sample corresponding to the composition shown in Run 3 of Table III was independently prepared, the percent weight loss at 350° C. after 10 minutes (step 1, line A) was 53.0 and at 600° C. after 5 minutes (step 2, line B) was 72.0. When compared to the graph of the FIGURE, the average percent carbon black was 14.6 which is in excellent agreement with the known value of 15.0.

We claim:

1. A method for thermogravimetrically analyzing a plastic molding composition comprising carbon black and a molding resin consisting of a homopolymer or copolymer of vinyl chloride determine the carbon black content wherein the method comprises the steps of:
    (a) compounding the plastic molding composition so that the carbon black is uniformly dispersed therein,
    (b) heating the molding composition in an inert atmosphere at about 350° C.,
    (c) maintaining the molding composition at about 350° C. in an inert atmosphere for a first given time which is long enough so that there is no further significant weight loss,
    (d) heating the molding composition in an inert atmosphere to a temperature between about 600° C. and 750° C.,
    (e) maintaining the molding composition at a temperature between about 600° and 750° C. in an inert atmosphere for a second given time which is long enough so that there is no further significant weight loss,
    (f) weighing the molding composition to determine the weight loss during the first given time and the second given time, and
    (g) comparing the weight loss with that for samples of known composition analyzed under the same conditions to determine the carbon black content of the molding composition.

2. A method in accordance with claim 1 comprising the additional step of maintaining the sample at a temperature between about 600° and 750° C. in an oxidizing atmosphere for a third given time which is long enough so that there is no further significant weight loss.

3. A method in accordance with claim 1 comprising the additional step of heating the mixture to about 50° C. in an inert atmosphere prior to step (b).

4. A method in accordance with claim 1 wherein the rate of heating for step (b) is between about 40° and 200° C. per minute.

5. A method in accordance with claim 4 wherein said rate is between about 160° and 200° per minute.

6. A method for thermogravimetrically analyzing a molded plastic article prepared from a plastic molding composition comprising carbon black and a molding resin consisting of a homopolymer or copolymer of vinyl chloride wherein the method comprises the steps of:
    (a) heating said article in an inert atmosphere to about 350° C;
    (b) maintaining the temperature at about 350° C. in an inert atmosphere for a first given time which is long enough so that there is no further significant weight loss;
    (c) heating the residue in an inert atmosphere to a temperature between about 600° and 750° C;
    (d) maintaining the temperature at between about 600° and 750° under an inert atmosphere for a second given time which is long enough so that there is no further significant weight loss;
    (e) weighing the residue to determine the weight loss during the first given time and the second given time; and
    (f) comparing the weight loss with that for samples of articles of known composition analyzed under the same conditions to determine the carbon black content of the article.

7. A method in accordance with claim 6, wherein the temperature in steps (c) and (d) is about 600° C.

8. A method in accordance with claim 6, wherein the rate of heating for steps (a) and (c) is between about 40° and 200° C. per minute.

9. A method in accordance with claim 8 wherein the rate of heating for steps (a) and (c) is between about 160° and 200° C. per minute.

* * * * *